US010822497B2

(12) United States Patent
Schmidt et al.

(10) Patent No.: US 10,822,497 B2
(45) Date of Patent: Nov. 3, 2020

(54) INTERFERENCE PIGMENTS

(71) Applicant: Merck Patent GmbH, Darmstadt (DE)

(72) Inventors: Christoph Schmidt, Kriftel (DE); Tanja Delp, Darmstadt (DE); Sabine Schoen, Herten (DE)

(73) Assignee: Merck Patent GmbH, Darmstadt (DE)

(*) Notice: Subject to any disclaimer, the term of this patent is extended or adjusted under 35 U.S.C. 154(b) by 12 days.

(21) Appl. No.: 15/086,750

(22) Filed: Mar. 31, 2016

(65) Prior Publication Data

US 2016/0222213 A1     Aug. 4, 2016

Related U.S. Application Data

(63) Continuation of application No. 11/052,898, filed on Feb. 9, 2005, now abandoned.

(30) Foreign Application Priority Data

Feb. 9, 2004 (DE) .................. 10 2004 006 360
Oct. 28, 2004 (DE) .................. 10 2004 052 544

(51) Int. Cl.
| C09C 1/00 | (2006.01) |
| C09D 5/36 | (2006.01) |
| C08K 9/10 | (2006.01) |
| A23G 3/36 | (2006.01) |
| A61Q 3/02 | (2006.01) |
| A61Q 19/10 | (2006.01) |
| A61K 8/29 | (2006.01) |

(52) U.S. Cl.
CPC ............ C09C 1/0021 (2013.01); A23G 3/362 (2013.01); A61K 8/29 (2013.01); A61Q 3/02 (2013.01); A61Q 19/10 (2013.01); C08K 9/10 (2013.01); C09C 1/0015 (2013.01); C09D 5/36 (2013.01); *A23V 2002/00* (2013.01); *C01P 2004/54* (2013.01); *C01P 2004/61* (2013.01); *C01P 2006/60* (2013.01); *C09C 2200/102* (2013.01); *C09C 2200/1004* (2013.01); *C09C 2200/1062* (2013.01); *C09C 2200/301* (2013.01); *C09C 2200/302* (2013.01)

(58) Field of Classification Search
CPC .. C07H 21/00; C01P 2004/54; C01P 2004/61; C01P 2006/60; C08K 9/10; C09C 1/0015; C09C 1/0021; C09C 2200/1004; C09C 2200/102; C09C 2200/1062; C09C 2200/301; C09C 2200/302; C09D 5/36
See application file for complete search history.

(56) References Cited

U.S. PATENT DOCUMENTS

| 4,086,100 A | 4/1978 | Esselborn |
| 4,456,486 A | 6/1984 | Bernhard |
| 4,565,581 A | 1/1986 | Bernhard |
| 6,056,815 A | 5/2000 | Fu et al. |
| 6,139,614 A | 10/2000 | Schmid et al. |
| 6,630,018 B2 | 10/2003 | Bauer |
| 6,656,259 B2 | 12/2003 | Pfaff |
| 6,689,205 B1 | 2/2004 | Bruckner et al. |
| 6,699,313 B2 | 3/2004 | Coulter et al. |
| 7,169,222 B2 | 1/2007 | Brückner |
| 7,226,503 B2 | 6/2007 | Anselmann |
| 7,344,590 B2 | 3/2008 | Schmidt |
| 2003/0039836 A1 | 2/2003 | Pfaff et al. |
| 2003/0047115 A1 | 3/2003 | Bauer et al. |
| 2003/0097965 A1 | 5/2003 | Heider et al. |
| 2004/0170838 A1 | 9/2004 | Ambrosius et al. |
| 2004/0221770 A1 | 11/2004 | Bruckner et al. |

FOREIGN PATENT DOCUMENTS

| CA | 2180669 A1 | 1/1997 |
| DE | 2522572 A1 | 12/1976 |
| DE | 3137808 A1 | 3/1983 |
| DE | 3151343 A1 | 7/1983 |
| EP | 0 735 545 A | 1/1997 |
| EP | 753545 A2 | 1/1997 |
| EP | 1281732 A1 | 2/2003 |
| EP | 1 469 041 A | 10/2004 |
| EP | 1469041 A2 | 10/2004 |
| EP | 753545 B2 | 5/2006 |
| JP | 2002294098 A | 10/2002 |
| JP | 2002294898 | 10/2002 |
| WO | 93/08237 A1 | 4/1993 |
| WO | 1993008237 A1 | 4/1993 |
| WO | 98/53011 A | 11/1998 |
| WO | 1998053011 A1 | 11/1998 |
| WO | 02/090448 A2 | 11/2002 |
| WO | 2002090448 A2 | 11/2002 |
| WO | 03/006558 A | 1/2003 |

OTHER PUBLICATIONS

English Abstract of JP 2002294898. Publication Date: Oct. 9, 2002. Inventor: Kuratnai Masato. JP Application No. JP 2001102409A. Filing Date: Mar. 30, 2001. Title: "Silky Lustrous Pigment". (Thomson Innovation Record Review.).
Glausch et al. "Perlglanzpigmente" 1996 ISBN 3878704291 ; pp. 14-25 and pp. 36-41.
Notice of Opposition in EP1564261 dated Feb. 23, 2017 (5 pages).
English language abstract for JP2002294098A assigned to TOPY IND published Oct. 9, 2002 (previously considered—corrected citation number).

*Primary Examiner* — Shuangyi Abu Ali
(74) *Attorney, Agent, or Firm* — Millen White Zelano and Branigan, PC; John Sopp

(57) ABSTRACT

The present invention relates to interference pigments based on transparent, low-refractive-index, flake-form substrates which have a high-refractive-index coating consisting of $TiO_2$ having a layer thickness of 20-200 nm and optionally an outer protective layer, and to the use thereof in paints, coatings, printing inks, security printing inks, plastics, button pastes, ceramic materials, glasses, for seed coloring, as dopants in the laser marking of plastics and papers, as additive for the laser welding of plastics, as additive for coloring in the foods and pharmaceuticals sectors, and in cosmetic formulations and for the preparation of pigment compositions and dry preparations.

17 Claims, No Drawings

INTERFERENCE PIGMENTS

The present invention relates to interference pigments having an intense color shift based on flake-form, transparent, low-refractive-index substrates and to the use thereof, in particular, in paints, coatings, printing inks, plastics, as dopants for the laser marking of plastics and papers, as additive in the foods and pharmaceuticals sectors, and in cosmetic formulations.

Luster or effect pigments are employed in many areas of industry, in particular in the area of automotive finishes, decorative coatings, plastics, paints, printing inks and in cosmetic formulations.

Owing to their color play, luster pigments, which exhibit an angle-dependent color change between a plurality of interference colors, are of particular interest for automotive finishes and in forgery-proof documents of value.

Mineral-based pearlescent pigments are of particular importance. Pearlescent pigments are produced by coating an inorganic, flake-form support with a high-refractive-index, usually oxidic layer. The color of these pigments is caused by wavelength-selective partial reflection and interference of the reflected or transmitted light at the medium/oxide or oxide/substrate interfaces.

The interference color of these pigments is determined by the thickness of the oxide layer, for example the hue of a green pigment is generated by a (in the optical sense) single high-refractive-index layer whose optical thickness causes a reflection maximum in the visible wavelength range at about 500 nm. This wavelength is perceived by the human eye as the color green. In the case of a first order maximum, however, the intensity curve is so broad that so much light is reflected throughout the region of visible light that the human eye perceives a very bright, but colorless impression.

According to the known rules—in particular from the coating of optical components—of the optical properties of thin layers, the intensity of the reflected light in an arrangement of a plurality of layers with alternating high and low refractive indexes increases greatly compared with a single layer. Thus, the application of a $TiO_2$—$SiO_2$—$TiO_2$ layer system to mica particles increases the intensity of the reflected light by about 60% compared with a $TiO_2$ single-layer system. Accordingly, the profile of the light reflected by interference is significantly more pronounced, so that an intense and bright reflection color must be expected for a multilayered system of this type. Pigments of this type are described in DE 196 18 569 A1.

The prior art discloses, for example, green interference pigments based on mica flakes. Mica flakes generally have a very broad scattering of the layer thickness and therefore have a neutral behaviour with respect to the interference color. Pearlescent pigments that have a single high-refractive-index coating on mica therefore represent single-layer optical systems, i.e. the interference color is determined exclusively by the layer thickness of the high-refractive-index metal-oxide layer. The coloristic design latitude of a mica/metal oxide green pigment is therefore very restricted. In addition, owing to their layer structure, mica particles have unevenness on the surface, which causes scattering and thus reduces the transparency and the coloristic quality of the product. In addition, mica exhibits a more or less pronounced grey-brown mass tone. This property further reduces the transparency and influences the absorption color of the application media in an undesired manner.

An object of the present invention is therefore to provide an interference pigment, in particular a green interference pigment, which is distinguished, in particular, by high transparency, a pure-white mass tone and a strong color flop which go beyond an exclusive color effect, for example green effect, blue effect, etc.

Upon further study of the specification and appended claims, further objects and advantages of this invention will become apparent to those skilled in the art.

Surprisingly, it has now been found that a specific transparent, low-refractive-index flake, such as, for example, an $SiO_2$ flake, coated with a thin $TiO_2$ layer causes a strong, for example a green, color impression and at the same time exhibits an extraordinary and intense color flop: the color shift does not necessarily, as is usual in the case of interference colors, take place from long-wave to short-wave colors, but can also take place in the opposite direction, for example from relatively short-wave green to relatively long-wave red. This is achieved by coating thin flakes, such as, for example, $SiO_2$ flakes, with a $TiO_2$ layer whose thickness is set precisely. Advantageous effects can be achieved by a precise combination of flake thickness and $TiO_2$ layer thickness.

Compared with mono-coated pigments (e.g., the single-layer optical systems discussed above) for example green pigments, based on mica, the pigments according to the invention exhibit the following properties:
 excellent transparency in the application medium
 pure-white mass tone
 strong, for example green, interference color
 very bright luster
 strong color shift
 given suitable combinations of the layer thicknesses of substrate and coating, it is possible to achieve a color shift from short-wave colors at a steep viewing angle to long-wave colors at a flat viewing angle, in particular from green to red in the case of green interference pigments.

In addition to these properties, the pigments according to the invention are distinguished over the known interference pigments by the following features:
 strong glitter effect
 tunable yellow-blue tint of the green color.

The said tint can be varied in broad ranges by setting the $TiO_2$ layer thickness and through the choice of the transparent flakes, such as, for example, $SiO_2$ flakes, of various thicknesses without the impression of an interference pigment being lost.

The invention therefore relates to highly chromatic, in particular green, interference pigments based on flake-form, transparent, low-refractive-index substrates which have a high-refractive-index coating consisting of $TiO_2$ having a layer thickness of 20-200 nm and optionally an outer protective layer.

The invention furthermore relates to the use of the interference pigments according to the invention in paints, coatings, printing inks, plastics, button pastes, ceramic materials, glasses, for seed coating, as additive for the laser welding of plastics, as dopants in the laser marking or laser welding of plastics and papers, as additive for coloring in the foods and pharmaceuticals sectors and in particular in cosmetic formulations. The pigments according to the invention are furthermore also suitable for the preparation of pigment compositions and for the preparation of dry preparations, such as, for example, granules, chips, pellets, briquettes, etc. The dry preparations are particularly suitable for printing inks and for cosmetic formulations.

Suitable base substrates for the interference pigments according to the invention are substrates preferably having a refractive index of <1.9, for example flake-form $SiO_2$ flakes, as described, for example, in WO 93/08237. Furthermore, besides the said SiO$_2$ flakes, and low refractive index, any flake-form, transparent substrate known to the person skilled in the art is suitable, such as, for example, Al$_2$O$_3$ flakes and glass flakes, natural or synthetic mica, and flake-form plastic particles. As discussed above, mica flakes will generally not meet the requirements but, if mica flakes can be provided which meet the transparency, low refractive index and narrow thickness distribution properties, they can be used in the invention. For example, synthetic mica flakes of fluorophlogopite can meet the requirements. Very particularly preferred substrates are SiO$_2$ flakes. The particular properties, such as the tuneable tint and in particular the angle dependence thereof, are effected to a crucial extent by a defined average thickness with a narrow thickness distribution.

The standard deviation (=percentage deviation of 66% of all individual measurement values from the calculated value for the average thickness) of the thickness of the substrate flakes should preferably be ≤15%, more preferably ≤10% and particularly preferably ≤6%, based on their average thickness.

The size of the base substrate is not crucial per se and can be matched to the particular application. In general, the flake-form transparent substrates have an average thickness (=sum of all thickness values/number of thickness measurements) of between 0.02 and 2 μm, preferably between 0.1 and 1 μm, in particular between 0.2 and 0.8 μm. The size in the other two dimensions is usually between 5 and 500 μm, preferably between 5 and 200 μm and in particular between 5 and 60 μm.

In order to achieve an intense color effect, for example a green or blue effect, with superimposed, angle-dependent tint, it is preferred that the average thickness of the individual flakes is within a standard deviation of ≤15%.

The aspect ratio (diameter/thickness ratio) of the substrate is preferably 1-1000, in particular 3-500 and very particularly preferably 5-200.

The thickness of the TiO$_2$ layer and of the substrate affect the optical properties of the pigment. The thicknesses of the layers can be set and matched to provide advantageous properties. The thickness of the TiO$_2$ layer is preferably 20-200 nm, more preferably 50-180 nm and in particular 70-160 nm.

The pigments according to the invention can be produced easily by the production of a high-refractive-index TiO$_2$ interference layer having a precisely defined thickness and a smooth surface on the finely divided, flake-form substrates. The TiO$_2$ can be in either rutile or anatase form. The TiO$_2$ is preferably in the rutile modification. Particular preference is given to SiO$_2$ flakes covered with a rutile TiO$_2$ layer. As is known in the art, a small amount of tin oxide can be incorporated to provide the rutile form of TiO$_2$.

Suitable low-refractive-index substrates are all inorganic and organic transparent materials which can be produced in the form of finely divided flakes having a narrow thickness distribution and have a refractive index of ≤1.8. Suitable organic substrates are, inter alia, polymers, such as, for example, polyesters (for example PET), polycarbonates, polyimides, polymethacrylates. Particularly preferred inorganic substrates are interference pigments, in particular based on SiO$_2$, Al$_2$O$_3$, flake-form single crystals, such as BiOCl and BN, and glass flakes, which may also be covered with a thin SiO$_2$ layer.

The metal-oxide TiO$_2$ layer is preferably applied by wet-chemical methods, it being possible to use the wet-chemical coating processes developed for the production of pearlescent pigments. Processes of this type are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017 or also in further patent documents and other publications known to the person skilled in the art.

In the case of wet coating, the substrate particles are suspended in water, and one or more hydrolysable titanium salts are added at a pH which is suitable for hydrolysis and which is selected in such a way that the metal oxides or metal oxide hydrates are precipitated directly onto the flakes without significant secondary precipitations occurring. The pH is usually kept constant by simultaneous metering-in of a base and/or acid. The pigments are subsequently separated off, washed and dried at 50-150° C. and, if desired, calcined for 0.1-3 h, it being possible for the calcination temperature to be optimised with respect to the particular coating present. In general, the calcination temperatures are between 250 and 1000° C., preferably between 350 and 950° C.

The coating can furthermore also be carried out in a fluidized-bed reactor by gas-phase coating, it being possible correspondingly to use, for example, the processes proposed in EP 0 045 851 A1 and EP 0 106 235 A1 for the production of pearlescent pigments.

The hue of the pigments can be varied in the very broad limits while maintaining the interference effect, for example green interference effect, through a different choice of the covering amounts or the resultant layer thicknesses. The angle-dependent color shift from, for example, green at steep viewing angles to red at flat viewing angles is substantially retained here. The hue variance relates, in particular, to the yellow and/or blue component. The fine tuning for a certain hue can be achieved beyond the pure choice of amount by approaching the desired color under visual or measurement technology control.

In order to increase the light, water and weather stability, it is frequently advisable to subject the finished pigment to post-coating or post-treatment, depending on the area of application. Suitable post-coatings or post-treatments are, for example, the processes described in German Patent 22 15 191, DE-A 31 51 354, DE-A 32 35 017 or DE-A 33 34 598. This post-coating further increases the chemical stability or simplifies handling of the pigment, in particular incorporation into various media. In order to improve the wettability, dispersibility and/or compatibility with the application media, functional coatings of Al$_2$O$_3$ or ZrO$_2$ or mixtures or mixed phases thereof can be applied to the pigment surface. Also possible are organic or combined organic/inorganic post-coatings, for example with silanes, as described, for example, in EP 0090259, EP 0 634 459, WO 99/57204, WO 96/32446, WO 99/57204, U.S. Pat. Nos. 5,759,255, 5,571, 851, WO 01/92425 or in J. J. Ponjeé, Philips Technical Review, Vol. 44, No. 3, 81 ff. and P. H. Harding J. C. Berg, J. Adhesion Sci. Technol. Vol. 11 No. 4, pp. 471-493.

The interference pigments according to the invention are simple and easy to handle. The pigments can be incorporated into the application system by simple stirring-in. Complex grinding and dispersal of the pigments is not necessary.

Since the interference pigments according to the invention combine high luster with high transparency and a pure-white mass tone, they enable particularly effective effects to be achieved in the various application media without the absorption color being significantly affected.

It goes without saying that, for the various applications, the interference pigments can also advantageously be used in the form of a mixture with organic dyes, organic pigments or other pigments, such as, for example, transparent and opaque white, colored and black pigments, and with flake-form iron oxides, organic pigments, holographic pigments, LCPs (liquid crystal polymers) and conventional transparent, colored and black luster pigments based on metal oxide-coated mica and $SiO_2$ flakes, etc. The interference pigments can be mixed in any ratio with commercially available pigments and fillers.

In the various applications, the pigment according to the invention can also be combined with further colorants of any type, for example organic and/or inorganic absorption pigments and dyes, multilayered interference pigments, such as, for example, Timiron®, Sicopearl® (BASF AG), Chroma-Flair® (Flex Products Inc.), BiOCl pigments, pearl essence or metal pigments, for example from Eckart. There are no limits to the mixing ratios and concentration.

The pigments according to the invention are compatible with a multiplicity of color systems, preferably from the areas of paints, coatings and printing inks. For the production of printing inks for, for example, gravure printing, flexographic printing, offset printing, and offset overprint varnishing, a multiplicity of binders, in particular water-soluble grades, are suitable, as marketed, for example, by BASF, Marabu, Pröll, Sericol, Hartmann, Gebr. Schmidt, Sicpa, Aarberg, Siegberg, GSB-Wahl, Follmann, Ruco or Coates Screen INKS GmbH. The printing inks can be water-based or solvent-based. The pigments are furthermore also suitable for the laser marking of paper and plastics and for applications in the agricultural sector, for example for greenhouse sheeting, and, for example, for the coloring of tent awnings.

The interference pigment according to the invention can be used for the pigmenting of surface coatings, printing inks, plastics, agricultural sheeting, seed coatings, food colorings, button pastes, medicament coatings or cosmetic formulations, such as lipsticks, nail varnishes, compact powders, shampoos, soaps, loose powders and gels. The concentration of the pigment mixture in the application system to be pigmented is generally between 0.1 and 70% by weight, preferably between 0.1 and 50% by weight and in particular between 0.5 and 10% by weight, based on the total solids content of the system. It is generally dependent on the specific application. In plastics comprising the green interference pigment according to the invention, preferably in amounts of from 0.01 to 50% by weight, in particular from 0.1 to 7% by weight, particularly pronounced sparkle effects can be achieved.

In the surface coatings sector, in particular in automotive finishes, the interference pigment is also employed for 3-coat systems in amounts of preferably 0.1-20% by weight, more preferably from 1 to 10% by weight.

In surface coatings, the interference pigment according to the invention has the advantage that the target gloss is achieved by a one-coat finish (one-coat system or base coat in 2-coat systems). Compared with finishes comprising, for example, a mica-based multilayered pigment or a conventional pearlescent pigment based on a substrate having a broad thickness distribution instead of the pigment according to the invention, finishes comprising the pigment according to the invention exhibit a clearer depth effect and a more pronounced luster effect.

The interference pigment according to the invention can also advantageously be employed in decorative and care cosmetics. The use concentration ranges from 0.01% by weight in shampoo to 100% by weight in the case of loose powders. In the case of a mixture of the interference pigments with spherical fillers, for example $SiO_2$, the concentration in the formulation can be 0.01-70% by weight. The cosmetic products, such as, for example, nail varnishes, compact powders, shampoos, loose powders and gels, are distinguished by particularly interesting color effects and an intense color shift. The color flop effect in nail varnish can be significantly increased compared with conventional nail varnishes with the aid of the pigments according to the invention.

Furthermore, the pigment according to the invention can be employed in bath additives, toothpastes and for the finishing of foods, for example mass coloring and/or coatings of boiled sweets, wine gums, such as, for example, jelly babies, pralines, liquorice, confectionery, sticks of rock, blancmange, fizzy drinks, sodas, etc., or as a coating, for example, in standard and coated tablets in the pharmaceuticals sector.

The pigment according to the invention can furthermore be mixed with commercially available fillers. Fillers which may be mentioned are, for example, natural and synthetic mica, nylon powder, pure or filled melamine resins, talc, glasses, kaolin, oxides or hydroxides of aluminum, magnesium, calcium, zinc, BiOCl, barium sulfate, calcium sulfate, calcium carbonate, magnesium carbonate, carbon, and physical or chemical combinations of these substances. There are no restrictions regarding the particle shape of the filler. It can be, for example, flake-form, spherical or needle-shaped in accordance with requirements.

It is of course also possible for the interference pigments according to the invention to be combined in the formulations with cosmetic raw materials and assistants of any type. These include, inter alia, oils, fats, waxes, film formers, preservatives and assistants which generally determine the technical properties, such as, for example, thickeners and rheological additives, such as, for example, bentonites, hectorites, silicon dioxides, Ca silicates, gelatines, high-molecular-weight carbohydrates and/or surface-active assistants, etc.

The formulations comprising the interference pigments according to the invention can belong to the lipophilic, hydrophilic or hydrophobic type. In the case of heterogeneous formulations having discrete aqueous and non-aqueous phases, the pigments according to the invention may in each case be present in only one of the two phases or alternatively distributed over both phases.

The pH values of the formulations can be between 1 and 14, preferably between 2 and 11 and particularly preferably between 5 and 8.

No limits are set for the concentrations of the pigments according to the invention in the formulation. They can be—depending on the application—between 0.001 (rinse-off products, for example shower gels) and 100% (for example gloss-effect articles for particular applications). The pigments according to the invention may furthermore also be combined with cosmetic active ingredients. Suitable active ingredients are, for example, insect repellents, UV A/BC protective filters (for example OMC, B3 and MBC), anti-ageing active ingredients, vitamins and derivatives thereof (for example vitamin A, C, E, etc.), self-tanning agents (for example DHA, erythrulose, inter alia), and further cosmetic active ingredients, such as, for example, bisabolol, LPO, ectoin, emblica, allantoin, bioflavonoids and derivatives thereof.

In the pigmenting of binder systems, for example for surface coatings and printing inks for gravure printing, offset printing or screen printing, or as precursors for printing inks, the use of the interference pigments according to the invention in the form of highly pigmented pastes, granules, pellets, etc., has proven particularly suitable. The pigment is generally incorporated into the printing ink in amounts of 2-35% by weight, preferably 5-25% by weight and in particular 8-20% by weight. Offset printing inks can comprise the pigments in amounts of up to 40% by weight or more. The precursors for printing inks, for example in the form of granules, as pellets, briquettes, etc., comprise up to 98% by weight of the pigment according to the invention in addition to the binder and additives. Printing inks comprising the pigment according to the invention exhibit purer hues, in particular green hues, than with conventional effect pigments. The particle thicknesses of the interference pigments according to the invention are relatively small and therefore cause particularly good printability.

The interference pigments according to the invention are furthermore suitable for the preparation of flowable pigment compositions and dry preparations, in particular for printing inks, comprising one or more pigments according to the invention, binders and optionally one or more additives.

The invention thus also relates to formulations comprising the interference pigment according to the invention.

The invention relates, in particular, to formulations which, besides the interference pigment according to the invention, comprise at least one constituent selected from absorbents, astringents, antimicrobial substances, antioxidants, antiperspirants, antifoaming agents, antidandruff active ingredients, antistatics, binders, biological additives, bleaching agents, chelating agents, deodorants, emollients, emulsifiers, emulsion stabilisers, dyes, humectants, film formers, odour substances, flavour substances, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

Example 1: Interference Pigment with Color Travel from Intense Green to Red 100 g of $SiO_2$ flakes (particle size 5-50 µm, average thickness 450 nm, standard deviation of the thickness: about 5%) are suspended in 2 l of deionised water and heated to 80° C. with vigorous stirring. A solution of 12 g of $SnCl_4 \times 5H_2O$ and 40 ml of hydrochloric acid (37%) in 360 ml of deionised water is metered into this mixture at pH 1.6. An amount of 460 ml of $TiCl_4$ solution (400 g of $TiCl_4$/l) is subsequently metered in at a pH of 1.6. The pH is kept constant during the addition of both the $SnCl_4 \times 5H_2O$ solution and $TiCl_4$ solutions using NaOH solution (32%). The pH is subsequently adjusted to 5.0 using sodium hydroxide solution (32%), and the mixture is stirred for a further 15 minutes.

For work-up, the pigment is filtered off, washed with 20 l of deionised water, dried at 110° C. and calcined at 850° C. for 30 min., giving an interference pigment having an intense, bright-green color, strong luster and high transparency. On changing to flat viewing angles, the pigment exhibits a red interference color.

USE EXAMPLES

Example A: Shower Gel

Phase A

| Raw material | Source | INCI | [%] |
|---|---|---|---|
| Pigment from Example 1 | Merck KGaA | | 0.10 |
| Keltrol T | Kelco | Xanthan Gum | 0.75 |
| Water, demineralised | | Aqua (Water) | 64.95 |

Phase B

| Raw material | Source | INCI | [%] |
|---|---|---|---|
| Plantacare 2000 UP | Cognis GmbH | Decyl Glucoside | 20.00 |
| Texapon ASV 50 | Cognis GmbH | Sodium Laureth Sulfate, Sodium Laureth-8 Sulfate, Magnesium Laureth Sulfate, Magnesium Laureth-8 Sulfate, Sodium Oleth Sulfate, Magnesium Oleth Sulfate | 3.60 |
| Bronidox L | Cognis GmbH | Propylene Glycol, 5-Bromo-5-Nitro-1,3-Dioxane | 0.20 |
| Everest 79658 SB perfume oil (deleted) | Haarmann & Reimer GmbH | Parfum | 0.05 |
| 1% FD&C Blue No. 1 in water | BASF AG | Aqua (Water), CI 42090 (FD&C Blue No. 1) | 0.20 |

Phase C

| Raw material | Source | INCI | [%] |
|---|---|---|---|
| Citric acid monohydrate | Merck KGaA/Rona ® | Citric Acid | 0.15 |
| Water, demineralised | | Aqua (Water) | 10.00 |

Preparation:

For phase A, stir the interference pigment into the water. Slowly scatter in the Keltrol T with stirring and stir until it has dissolved. Add phases B and C one after the other while stirring slowly until everything is homogeneously distributed. Adjust pH to 6.0 to 6.4.

Example B: Nail Varnish

| Raw material | Source | INCI | [%] |
|---|---|---|---|
| Pigment from Example 1 | Merck KGaA | | 2.00 |
| Thixotropic nail varnish base 1348 | International Lacquers S.A. | Toluene, Ethyl Acetate, Butyl Acetate, Nitrocellulose, Tosylamide/Formaldehyde Resin, Dibutyl Phthalate, Isopropyl Alcohol, Stearalkonium Hectorite, Camphor, Acrylates Copolymer, Benzophenone-1 | 98.00 |

Preparation:

The interference pigment is weighed out together with the varnish base, mixed well manually using a spatula and subsequently stirred at 1000 rpm for 10 min.

Example C: Surface Coating System

90% by weight of Hydroglasur BG/S colorless (waterborne varnish from Ernst Diegel GmbH)
10% by weight of green interference pigment from Example 1
Coating by spraying at 80° C.
5 min predrying at 80° C.
20 min baking at 180° C.

Example D: Plastic 1 kg of polystyrene granules is wetted uniformly with 5 g of adhesive in a tumble mixer. 42 g of green interference pigment from Example 1 are then added and mixed for 2 minutes. These granules are converted into stepped plates having the dimensions 4×3×0.5 cm under conventional conditions in an injection-moulding machine. The stepped plates are distinguished by their pronounced sparkle effect.

Example E: Coloring of Confectionery

Crude product: effervescent sweets white
Spray solution:
94% of alcoholic shellac solution from Kaul
6% of green interference pigment from Example 1
The effervescent sweets are sprayed with an interference pigment/shellac solution until the desired color application has been reached. Subsequent drying with cold air is possible.

The entire disclosures of all applications, patents and publications, cited herein and of corresponding German application Nos. 10 2004 05 2544.7, filed Oct. 28, 2004 and 10 2004 006 360.5 filed Feb. 9, 2004, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An interference pigment, which consists of a low-refractive-index, transparent, flake substrate having only one high-refractive-index coating consisting essentially of $TiO_2$ having a layer thickness of 70-160 nm and optionally further coated with an outer protective layer,
wherein the pigment exhibits a color flop from the short wave color green at a steep viewing angle to the long wave color red at a flat viewing angle,
wherein the substrate has an average thickness of 0.2 to 0.8 μm and a size in the other two dimensions of between 5 and 60 μm,
wherein the standard deviation of the thickness of the substrate flakes is 15%, based on their average thickness, and
wherein the $TiO_2$ is in the rutile modification and optionally contains an amount of tin oxide sufficient to provide it in the rutile modification.

2. An interference pigment according to claim 1, wherein the standard deviation of the thickness of the flake substrate is ≤10%, based on their average thickness.

3. An interference pigment according to claim 1, wherein the transparent flake is an $SiO_2$ flake, $Al_2O_3$ flake, natural or synthetic mica flake or a glass flake.

4. An interference pigment according to claim 3, wherein the transparent flake is an $SiO_2$ flake.

5. A process for the production of the interference pigment of claim 1, comprising, coating the substrate by a wet-chemical method by hydrolytic decomposition of a titanium metal salt in aqueous medium or by thermal decomposition by a CVD or PVD process.

6. A pigment composition comprising one or more binders, optionally one or more additives and one or more interference pigments according to claim 1.

7. A dry preparation in the form of pellets, granules, chips, or briquettes, comprising one or more interference pigments according to claim 1.

8. The interference pigment of claim 1, wherein the substrate has a refractive index of ≤1.8.

9. A paint, button paste, coating, printing ink, security printing ink, plastic, ceramic material, glass, seed coating, dopant for the laser marking of plastics and papers, additive for the laser welding of plastics, additive for food or pharmaceutical coloring, or cosmetic, which comprises an interference pigment of claim 1.

10. The interference pigment of claim 1, wherein the pigment has no outer protective layer.

11. The interference pigment of claim 1, wherein the pigment has an outer protective layer.

12. An interference pigment, which consists of a low-refractive-index, transparent, $SiO_2$ flake substrate having only one high-refractive-index coating consisting essentially of $TiO_2$ having a layer thickness of 20-200 nm and optionally further coated with an outer protective layer,
wherein the pigment exhibits a color flop from green at a steep viewing angle to red at a flat viewing angle,
wherein the substrate has an average thickness of 0.1 to 1 μm and a size in the other two dimensions of between 5 and 60 μm,
wherein the standard deviation of the thickness of the substrate flakes is 15%, based on their average thickness, and
wherein the $TiO_2$ is in the rutile modification and optionally contains an amount of tin oxide sufficient to provide it in the rutile modification.

13. An interference pigment according to claim 1, wherein the thickness of the high-refractive-index coating is matched to the average thickness of the flake substrate.

14. The interference pigment of claim 12, wherein the high-refractive-index coating consisting essentially of $TiO_2$ has a layer thickness of 50 to 180 nm.

15. The interference pigment of claim 12, wherein the high-refractive-index coating consisting essentially of $TiO_2$ has a layer thickness of 70 to 160 nm.

16. The pigment composition of claim 6, which comprises at least one additive selected from absorbents, astringents, antimicrobial substances, antioxidants, antiperspirants, antifoaming agents, antidandruff active ingredients, antistatics, biological additives, bleaching agents, chelating agents, deodorants, emollients, emulsifiers, emulsion stabilisers, dyes, humectants, film formers, odour substances, flavour substances, insect repellents, preservatives, anticorrosion agents, cosmetic oils, solvents, oxidants, vegetable constituents, buffer substances, reducing agents, surfactants, propellent gases, opacifiers, UV filters, UV absorbers, denaturing agents, viscosity regulators, perfumes and vitamins.

17. An interference pigment, which consists of a low-refractive-index, transparent, $SiO_2$ flake substrate having only one high-refractive-index coating consisting essentially of $TiO_2$ having a layer thickness of 70-160 nm and optionally further coated with an outer protective layer,
  wherein the pigment exhibits a color flop from the short wave color green at a steep viewing angle to the long wave color red at a flat viewing angle,
  wherein the substrate has an average thickness of 0.2 to 0.8 µm and a size in the other two dimensions of between 5 and 60 µm,
  wherein the standard deviation of the thickness of the substrate flakes is 10%, based on their average thickness,
  wherein the thickness of the high-refractive-index coating is matched to the average thickness of the flake substrate, and
  wherein the $TiO_2$ is in the rutile modification and optionally contains an amount of tin oxide sufficient to provide it in the rutile modification.

* * * * *